(12) United States Patent
Evers et al.

(10) Patent No.: US 12,336,712 B2
(45) Date of Patent: Jun. 24, 2025

(54) FASTENING DEVICES AND RELATED METHODS OF USE

(71) Applicant: Boston Scientific Scimed, Inc., Maple Grove, MN (US)

(72) Inventors: Ryan Evers, Billerica, MA (US); Michael S. H. Chu, Brookline, MA (US); Paul Smith, Smithfield, RI (US); Narunn Suon, Lawrence, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 18/635,798

(22) Filed: Apr. 15, 2024

(65) Prior Publication Data
US 2024/0252174 A1 Aug. 1, 2024

Related U.S. Application Data

(63) Continuation of application No. 17/514,727, filed on Oct. 29, 2021, now Pat. No. 11,986,186.
(Continued)

(51) Int. Cl.
*A61B 17/10* (2006.01)
*A61B 17/00* (2006.01)
(Continued)

(52) U.S. Cl.
CPC ............. *A61B 17/10* (2013.01); *A61B 17/08* (2013.01); *A61B 34/71* (2016.02);
(Continued)

(58) Field of Classification Search
CPC ....... A61B 17/10; A61B 17/08; A61B 17/083; A61B 17/122; A61B 17/1285;
(Continued)

(56) References Cited

U.S. PATENT DOCUMENTS

| 8,333,780 B1 * | 12/2012 | Pedros ................... A61B 34/30 606/174 |
| 8,690,899 B2 | 4/2014 | Kogiso et al. |

(Continued)

FOREIGN PATENT DOCUMENTS

| EP | 2428169 B1 | 10/2016 |
| EP | 3638092 B1 | 6/2021 |

(Continued)

*Primary Examiner* — Kankindi Rwego
(74) *Attorney, Agent, or Firm* — Bookoff McAndrews PLLC (57) ABSTRACT

A medical device, comprising a fastening assembly, wherein the fastening assembly includes an adapter defining an opening therethrough, a fastener releasably coupled to the adapter, wherein the fastener includes at least two jaws pivotable relative to one another, the fastener having a first configuration wherein the jaws are open and a second configuration wherein the jaws are closed, and at least one cable coupled to the fastener and the adapter, the at least one cable being configured to apply tension to the fastener to transition between the first configuration and the second configuration while the fastener is coupled to the adapter, and to control release of the fastener from the adapter.

20 Claims, 8 Drawing Sheets

Related U.S. Application Data (60) Provisional application No. 63/108,536, filed on Nov. 2, 2020.

(51) Int. Cl.
*A61B 17/08* (2006.01)
*A61B 34/00* (2016.01)

(52) U.S. Cl.
CPC .......... *A61B 2017/0034* (2013.01); *A61B 2017/00486* (2013.01); *A61B 2034/715* (2016.02)

(58) Field of Classification Search
CPC . A61B 17/2841; A61B 17/2909; A61B 34/71; A61B 2017/0034; A61B 2017/00486; A61B 2017/00296; A61B 2034/715; A61B 2090/037; A61B 17/128; A61B 2017/0488

USPC .................................................. 606/139, 142
See application file for complete search history.

(56) References Cited

U.S. PATENT DOCUMENTS

| | | | |
|---|---|---|---|
| 2004/0097982 A1* | 5/2004 | Jugenheimer | A61B 17/1227 606/151 |
| 2005/0107809 A1 | 5/2005 | Litscher et al. | |
| 2011/0208210 A1 | 8/2011 | Baur et al. | |
| 2017/0014135 A1* | 1/2017 | Martin | A61B 17/1285 |
| 2019/0298400 A1* | 10/2019 | Horeman | A61B 17/29 |
| 2020/0397445 A1 | 12/2020 | Shikhman et al. | |

FOREIGN PATENT DOCUMENTS

| | | |
|---|---|---|
| WO | 0135832 A2 | 5/2001 |
| WO | 2019135958 A2 | 7/2019 |

* cited by examiner

FASTENING DEVICES AND RELATED METHODS OF USE

CROSS-REFERENCE TO RELATED APPLICATIONS

This application is a continuation of U.S. application Ser. No. 17/514,727, filed Oct. 29, 2021, which claims the benefit of priority from U.S. Provisional Application No. 63/108,536, filed on Nov. 2, 2020, each of which is incorporated by reference herein in its entirety.

TECHNICAL FIELD

This disclosure relates generally to tissue fastening. More particularly, the present disclosure includes fastening mechanisms for medical devices and related methods of using the fastening mechanisms.

BACKGROUND

Interventional and therapeutic procedures oftentimes require closure of a tissue site, e.g., the gastrointestinal tract wall, as part of the procedure. Closure may be accomplished via the use of a fastening component, e.g., a clip or staple. The fastening component may be delivered to a site through a channel of a medical device, e.g., an endoscope, or may be attached over the scope. An issue with common over-the-scope fastening components is the quick deployment of the fastener to the targeted tissue site, without the ability unfasten and reposition the fastener to a more desired or correct site.

SUMMARY OF THE DISCLOSURE

According to an example, a medical device may comprise a fastening assembly, wherein the fastening assembly includes an adapter defining an opening therethrough, a fastener releasably coupled to the adapter, wherein the fastener includes at least two jaws pivotable relative to one another, the fastener having a first configuration wherein the jaws are open and a second configuration wherein the jaws are closed, and at least one cable coupled to the fastener and the adapter, the at least one cable being configured to apply tension to the fastener to transition between the first configuration and the second configuration while the fastener is coupled to the adapter, and to control release of the fastener from the adapter.

In another example, the adapter may be a tubular shape configured to receive a distal end of a shaft. The adapter may include a resistance element coupled to the fastener, wherein the resistance element biases the fastener towards the first configuration, and wherein a tension force applied to the at least one cable transitions the fastener towards the second configuration against the bias of the resistance element. In the second configuration, the jaws of the fastener may extend along planes parallel to each other. The fastener may be biased towards the second configuration. Each of the at least two jaws may include at least one edge configured to grip or penetrate tissue. The fastener may include a first jaw coupled to a second jaw at each of a first pivot and a second pivot.

In another example, the at least one cable may include a first cable and a second cable. The first cable may be coupled to the first pivot and the second cable is coupled to the second pivot, wherein tensioning the first cable and the second cable pivots the first jaw relative to the second jaw. The at least one cable may include a frangible portion, the frangible portion being attached to the fastener and the adapter, and wherein breaking the frangible portion by tensioning the at least one cable releases the fastener from the adapter. A tensioning force sufficient to break the frangible portion may be greater than a tensioning force sufficient to transition the fastener between the first configuration and the second configuration.

In another example, the medical device may further include a shaft and a handle operably coupled to a proximal end of the shaft, wherein the adapter is coupled to a distal portion of the shaft and the at least one cable extends through the shaft from the adapter to the handle.

According to another example, a medical device may comprise a fastening assembly, wherein the fastening assembly includes an adapter, a fastener releasably coupled to the adapter, wherein the fastener includes a first jaw pivotable relative to a second jaw, the first jaw and the second jaw being open in a first configuration of the fastener and closed in a second configuration of the fastener, a first cable coupled to the fastener, wherein tensioning the first cable transitions the fastener between the first configuration and the second configuration, and a second cable coupled to the fastener or the adapter, wherein tensioning the second cable releases the fastener from the adapter. Tensioning the second cable may translate the fastener distally relative to the adapter. The medical device may further comprise a shaft, a connector, and a handle operably coupled to a proximal end of the shaft, wherein the adapter is coupled to a distal portion of the connector, the connector is coupled to a distal portion of the shaft, and the first and second cables extend proximally through the connector from the adapter to the handle. The medical device may further comprise a spring within the lumen of the connector adjacent to the adapter. Tensioning the second cable may move the adapter proximally, against a resistance of the spring. The proximal movement of the adapter may shear the first cable from the fastener, thereby releasing the fastener from the adapter. The connector may include an opening and a tube fixed to a proximal surface of the connector, wherein the tube is configured to receive the first cable and the second cable extending through a lumen of the connector and the opening.

According to an example, a method of fastening tissue may comprise inserting a medical device into a natural orifice of a subject, wherein the medical device includes a fastening assembly coupled to a distal portion of a shaft of the medical device, the fastening assembly including a fastener, an adapter, and at least one cable coupled to the fastener and the adapter, positioning the fastening assembly adjacent to a target site, applying tension to the at least one cable to close the fastener onto tissue at the target site while the fastener is coupled to the adapter, and applying further tension to the at least one cable to release the fastener from the adapter.

BRIEF DESCRIPTION OF THE DRAWINGS

The accompanying drawings, which are incorporated in and constitute a part of this application, illustrate various exemplary embodiments and together with the description, serve to explain the principles of the present disclosure through exemplary embodiments.

DETAILED DESCRIPTION

Reference will now be made in detail to aspects of the disclosure, examples of which are illustrated in the accompanying drawings. Wherever possible, the same or similar reference numbers will be used through the drawings to refer to the same or like parts. The term "distal" refers to a portion farthest away from a user when introducing a device into a subject (e.g., a patient). By contrast, the term "proximal" refers to a portion closest to the user when placing the device into the subject.

Both the foregoing general description and the following detailed description are exemplary and explanatory only and are not restrictive of the features, as claimed. As used herein, the terms "comprises," "comprising," "having," "including," or other variations thereof, are intended to cover a non-exclusive inclusion such that a process, method, article, or apparatus that comprises a list of elements does not include only those elements, but may include other elements not expressly listed or inherent to such a process, method, article, or apparatus. In this disclosure, relative terms, such as, for example, "about," "substantially," "generally," and "approximately," are used to indicate a possible variation of ±10% in a stated value or characteristic.

Embodiments of this disclosure may address one or more of the limitations in the art. The scope of the disclosure, however, is defined by the attached claims and not the ability to solve a specific problem. The disclosure is drawn to medical devices including fastening mechanisms, and related methods, among other aspects.

An exemplary medical system may include, as an example, a suitable scope (e.g., bronchoscope, duodenoscope, endoscope, colonoscope, ureteroscope, etc.), catheter, tool, instrument, or the like, having a shaft/catheter that extends distally from a handle to a distal portion of the device. The shaft of such medical devices may be any suitable flexible shaft configured to traverse bodily lumens during a medical procedure. The shaft may include at least one lumen for receiving additional devices, e.g., scopes, tools, instruments, cables, or the like. Thus, the shaft may serve as a sheath or a guide for the aforementioned additional devices, which may extend distally through the shaft. Similarly, the handle may be any suitable medical device handle. The handle may include components for actuating or otherwise controlling the medical device, tools or devices associated with medical device, and/or the fastening mechanism(s) of the medical device.

The fastening mechanism may include an adapter, a fastener, and control members or elements (e.g., control cables or wires, etc.). The adapter is any suitable component that may be coupled to a distal end of the shaft. The adapter may comprise any suitable biocompatible material or combination of materials. The manner by which the adapter may be coupled to a distal end of a shaft of a scope or other suitable medical device may depend on the shape of the adapter. For example, in some examples, the adapter may be generally cylindrical or tube-shaped, including a longitudinal opening. The dimensions may be selected so that the adapter may be fitted over a distal portion of the shaft/scope, e.g., wherein the opening may be of such a diameter so that the adapter is fitted tightly/snugly over said shaft. In another example, the dimensions of a generally cylindrical or tube shaped adapter may be selected so that the adapter may be securely fitted within a distal opening of a shaft. Thus, the adapter may be any suitable shape that may couple to a distal portion of a shaft. The adapter may further include additional components and features that may assist in holding a fastener, in its pre-deployed state, as further discussed below.

The fastener may be configured as a clip or staple, for example. Exemplary materials suitable for the fastener include biocompatible metals and metal alloys such as, e.g., stainless steel, nitinol, etc. The fastener may include at least one jaw, e.g., two, three, or more jaws, etc., which may include features for grasping or otherwise securing tissue. For example, the fastener may include two jaws, each of which may include one or more edges or teeth, e.g., one, two, three, etc., configured to penetrate the targeted tissue. In some examples, the fastener includes two jaws that are separate components coupled to one another, via a pair of suitable pivots/hinges. In some examples, the fastener includes two jaws formed from a single piece, wherein the single piece is further molded or shaped to form pivots between the two jaws, e.g., in the manner of a living hinge. In such examples wherein the fastener includes two jaws, the two jaws may pivot relative to one another, individually or simultaneously, and the fastener may be in an open (e.g., pre-deployed) state or a closed (e.g., deployed) state.

Thus, for example, the fastener may be capable of transitioning between different configurations in order to deploy the fastener in tissue and reposition the fastener before complete deployment, as further discussed below. The fastener may be configured to adopt a flat state wherein the jaw(s) are closed, and an arched state wherein the jaw(s) may be either open or closed. The jaw(s) of the fastener may be biased to adopt a closed, flat state. In the default flat state of a fastener having two jaws and two pivots at respective junctions between the jaws, the fastener may be relatively linear from one pivot to the other pivot, so that the fastener extends along a plane that includes both pivots. In the arched state, the fastener, regardless of the jaws being open or closed, may be bent or arched at a mid-point between the pivots so that the pair of pivots face one another. Such fasteners may comprise a flexible, elastic material, e.g., nitinol, to allow the fastener to adopt the arched shape, while having sufficient strength to fasten on to tissue. The fastener, in the arched state, may be mounted onto an adapter so that the pivots are secured or coupled onto a distal portion of the adapter. Thus, the arched state may represent a pre-deployment state of the fastener, whereas the flat state may represent a deployed state of the fastener. The fastener, which may comprise an elastic material, may transition from the arched state to its pre-deployment, default state, such that the pivots rotate from being perpendicular to the jaws to being co-planar with the jaws.

The control members may be any suitable cables or wires, e.g., steel cables, coupling the fastener to the handle of the medical device. For example, control cables may connect the fastener to features or aspects of the handle that may be actuated to apply tension onto the control cables. The tensioning and relaxation of the control cables may transition the fastener between an open and closed state.

Control cables may also assist in maintaining the fastener onto the adapter, prior to the fastener's deployment. For example, one pair, two pairs, or three or more pairs of control cables may be used to actuate the fastener during deployment. In some examples, to deploy the fastener, the portions of the control cables holding the fastener may be shearable or frangible, so that the fastener may be released when sufficient tension is applied to the cables.

Figure 1:
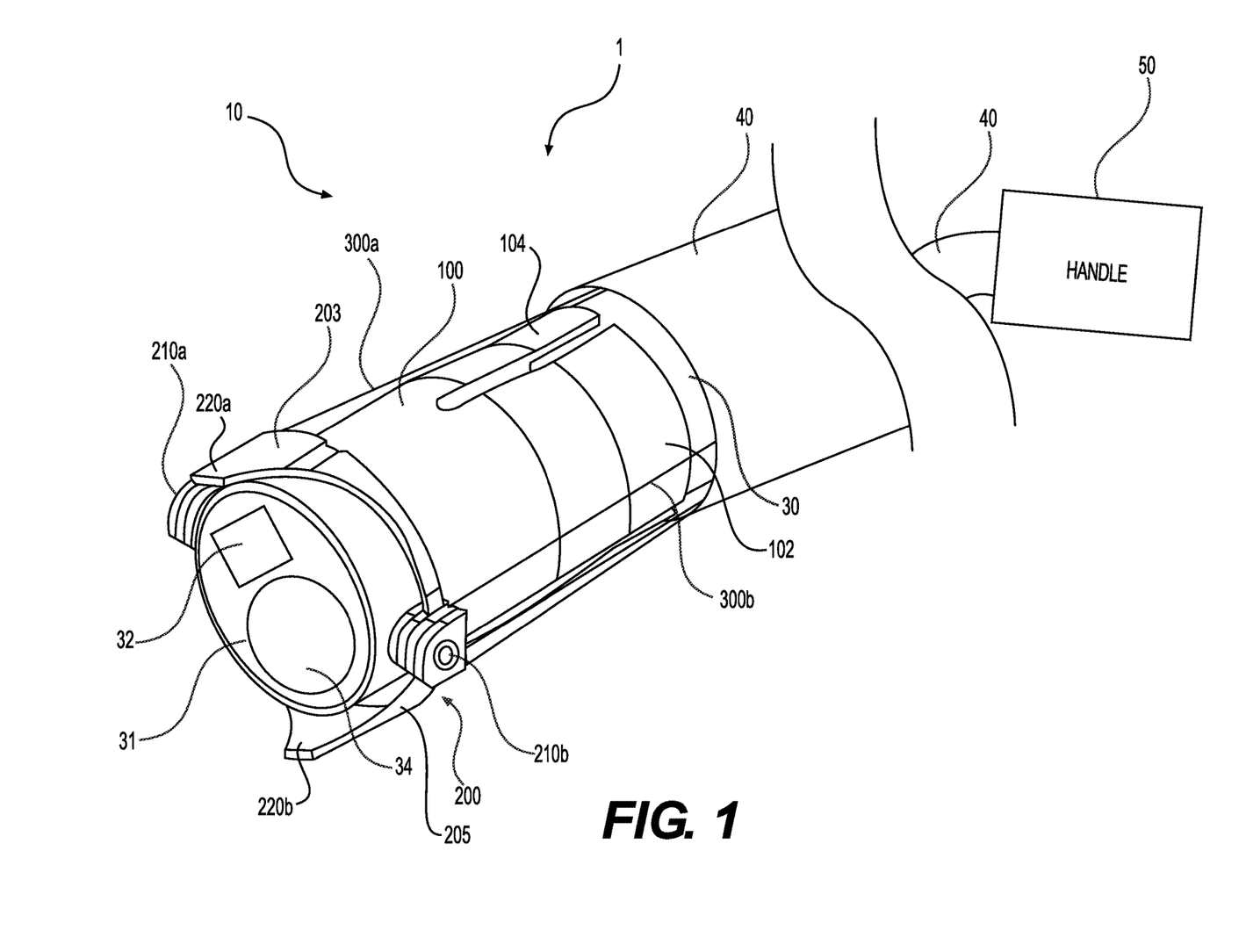
FIG. 1 is a perspective view of a medical device, according to some aspects of this disclosure.

Referring to an exemplary system shown in FIG. 1, a medical device 1, e.g., an endoscope, is shown. Medical device 1 includes a sheath 40, a handle 50 coupled to a proximal portion of sheath 40, and a shaft 30, shaft 30 extending through sheath 40, and fastening component 10 mounted over a distal portion of scope 30. It is noted that fastening component 10 is not limited to being mounted over shaft 30, as shown in the examples of FIG. 1. In some embodiments, fastening component 10 may be mounted over other devices extending through shaft 30, or may be mounted on sheath 40 itself. It is also noted, the device 1 may be without sheath 40.

Handle 50 may include at least one aspect for actuating or controlling medical device 1, e.g., shaft 30, and for transitioning a fastener 200 between open and closed states in order to deploy fastener 200. Sheath 40 may be flexible and cover at least a portion of shaft 30. Shaft 30 may extend from handle 50 to a distal portion or end of medical device 1. As discussed above, shaft 30 may be any suitable biocompatible and flexible shaft. As shown in FIG. 1, shaft 30 includes a lumen defining a working channel 34, through which accessory devices or instruments may be introduced. Shaft 30 further includes an imager 32 at a distal end 31 of shaft 30. Imager 32 may be any suitable imaging component.

Fastening component 10 includes an adapter 100, fastener 200, e.g., a clip, and a pair of cables 300a, 300b. Adapter 100 as shown is tubular in shape, including a longitudinal opening with suitable dimensions for receiving a distal portion of scope, so that adapter 100 may be fitted over the distal portion of shaft 30. Adapter 100 may include an opening of any suitable diameter that allows adapter 100 to have a snug or friction fit over shaft 30, and minimize the displacement of adapter 100 with respect to shaft 30.

The proximal portion of adapter 100 may be segmented circumferentially, and each segment, e.g., segments 102, 104, may be flexible and biased radially inwards. Thus, the proximal opening of adapter 100 may be of a smaller diameter than that of shaft 30, but still be able to receive shaft 30, as each of the segments (e.g., 102, 104) flex outwards to receive shaft 30. Adapter 100 also includes a pair of projections, shown as pegs 110a, 110b (shown in FIG. 2A), extending outwards from a distal portion of adapter 100. Pegs 110a, 110b are on directly opposite sides of adapter 100, and are configured to assist in maintaining fastener 200 onto adapter 100.

Figure 2A:
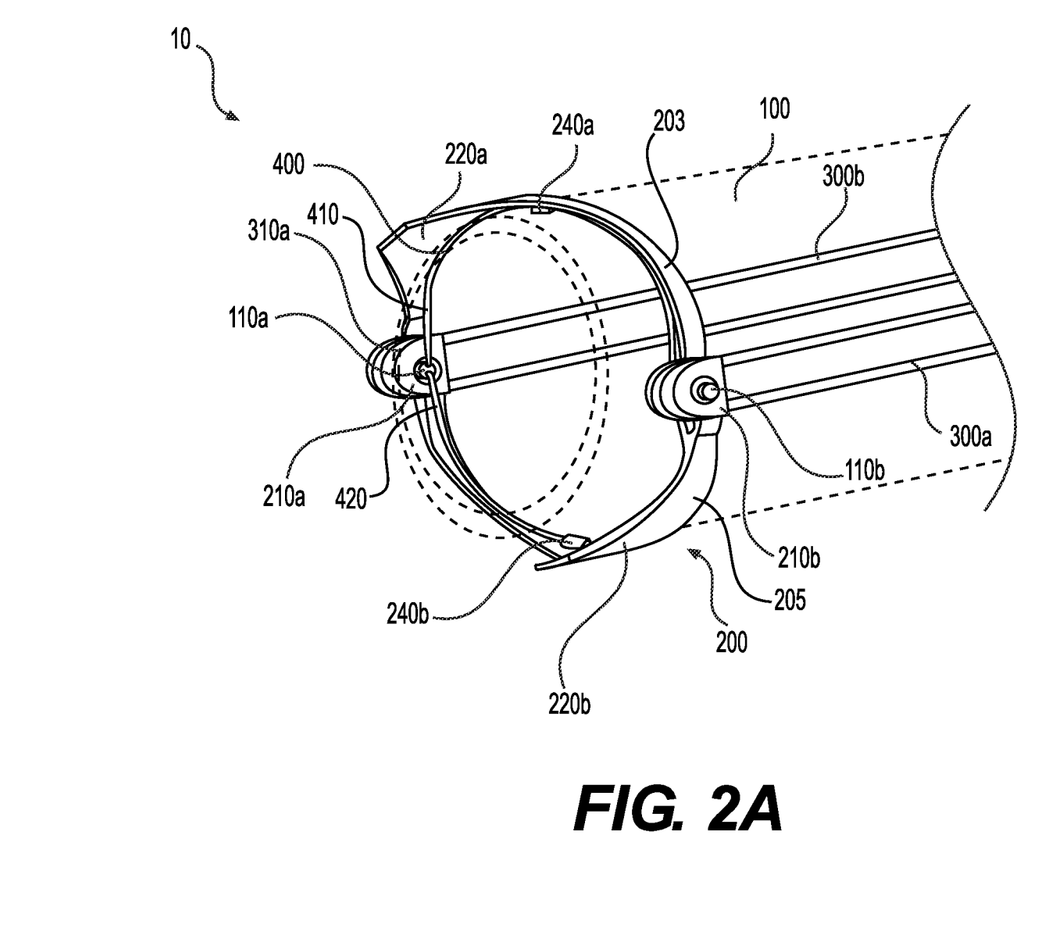
FIG. 2A is a perspective view of an adapter of the medical device of FIG. 1.
Figure 2B:
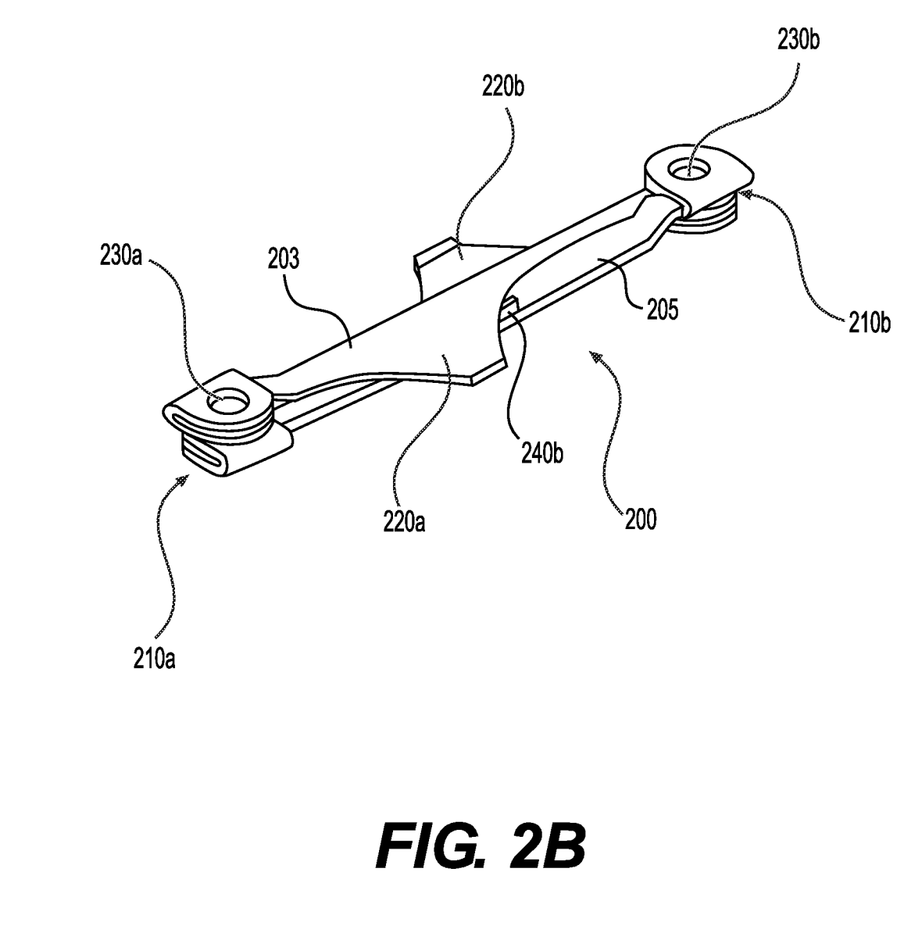
FIG. 2B is a perspective view of a fastener of the medical device of FIG. 1.

Adapter 100 further includes a resistive feature, e.g., a hoop 400, as shown in FIG. 2A. Hoop 400 may comprise two wires or cables 410, 420 formed of any suitable material providing sufficient flexibility. For example, cables 410, 420 may comprise a nickel based alloy, a titanium based alloy, nitinol, medium to high carbon steels, spring steel, stainless steel, Inconel, and/or Elgiloy. As illustrated, hoop 400 is coupled to pegs 110a, 110b. Cable 410 extends between pegs 110a, 110b in a curved, semi-circular manner. Cable 420 also extends between pegs 110a, 110b in the same manner as cable 410, but towards the opposite direction. Thus, cable 410 and cable 420 collectively form a hoop-like shape. Hoop 400 is biased towards a first, open state, in which cables 410, 420 are transverse, e.g., perpendicular, to a longitudinal axis of adapter 100. However, hoop 400 may flex when a sufficient force is applied against cables 410 and 420. For example, cables 410 and 420 may be flexed towards a distal direction so that cables 410, 420 pivot towards one another, thereby transitioning into a second, closed state. Hoop 400 may be coupled to fastener 200 and bias fastener 200 in an arched, open state, as shown in FIG. 2B and described in further detail below.

As discussed above, fastener 200 may transition between an arched state and a default, flat state. FIG. 1 and FIG. 2A illustrate fastener 200 mounted onto adapter 100 while in an open, arched state. Fastener 200 includes a first jaw 203 and a second jaw 205. First jaw 203 and second jaw 205 each include a single tooth 220a, 220b, both of which are configured to penetrate a targeted site. It is noted that the shape of teeth 220a and 220b illustrated in the figures is exemplary only. For example, teeth 220a, 220b are shows as truncated ridges positioned proximate a mid-point of each jaw 203, 205. In other examples, the ridges may be pointed and/or may have multiple peaks that are truncated or pointed. Further, each jaw 203, 205 may include a single tooth 220a, 220b as shown, or one or both jaw 203, 205 may include two or more teeth, e.g., two, three, or four or more teeth.

As shown, the ends of first jaw 203 are coupled to corresponding ends of second jaw 205 by a pair of pivots/hinges 210a and 210b. Thus, pivot 210a and pivot 210b enable jaws 203, 205 to pivot relative to each other, when fastener 200 is in an arched state. Pivot 210 and pivot 210b may each include a central opening 230a and 230b (shown in FIG. 2B). Central openings 230a, 230b may be configured to receive corresponding projections of adapter, e.g., pegs 110a, 110b, thereby allowing fastener 200 to be mounted onto adapter 100.

A proximal portion of the inner surfaces of jaws 203 and 205 may respectively include hooks 240a, 240b. Hooks 240a and 240b protrude radially inwards towards adapter 100. Hooks 240a, 240b are of a curved shape or rounded shape, e.g., c-shaped, so that they may grasp onto hoop 400. The open or receiving ends of hooks 240a, 240b may be proximal facing so that the distal facing surface of hoop 400 is adjacent to hooks 240a, 240b. In some examples, hooks 240a, 240b may approach the open or receiving ends from an edge of adapter 100, e.g., a proximal or distal edge, or an intermediate portion of adapter 100. In some examples, hooks 240a, 240b may be more rigidly shaped, e.g., square-shaped, L-shaped, or angled than as depicted in FIG. 2A.

Hooks 240a, 240b may assist in further securing fastener 200 onto adapter 100 while fastener 200 is in an open, arched state. Moreover, hooks 240a, 240b couple fastener 200 to hoop 400 so that fastener 200 is biased towards an arched and open state. By application of a sufficient force onto jaws 203, 205, fastener 200 may transition towards a closed state, against the resistance provided by hoop 400, and eventually a flat, deployed state. Such force may be applied onto fastener 200 by cables 300a, 300b, described in further detail below.

The default, flat state of fastener 200 is shown in FIG. 2B. In the flat state, fastener 200 is closed so that jaws 203 and 205 cross and are adjacent to one another. Furthermore, fastener 200 is relatively linear in shape, from one pivot 210a, 210b, to the other pivot 210a, 210b. The surfaces of pivots 210a, 210b may be co-planar in this configuration. In the flat state, fastener 200 is deployed and released from adapter 100 and cables 300a, 300b. An example of deploying fastener 200 is discussed below. It is noted that a flat fastener 200 may provide one or more benefit during a medical procedure including, but not limited to, serving as a tamponade to active bleeding, providing a low profile closure of a defect to pass a medical device (e.g., endoscope) beyond the repaired area without disruption to fastener 200 and the site, a constant closure force, and/or having a low delivered profile thereby allowing navigation past the area of tissue being clipped or otherwise fastened.

Cables 300a and 300b may be any suitable tensioning control elements, e.g., steel cables, each including both a first end and second end coupled to handle 50. As shown in FIG. 1 and FIG. 2A, cables 300a and 300b may respectively be routed around pivots 210a, 210b so both ends of cables 300a and 300b return proximally to handle 50, through a lumen of sheath 40. The first and second ends of both cables 300a and 300b may connect to components of handle 50 such as control knobs, levers, or other control features, which may be actuated to apply tension onto cables 300a and 300b.

Cables 300a and 300b may be routed so that the tension applied to cables 300a, 300b causes jaws 203, 205 to pivot relative to one another, thereby transitioning fastener 200 towards a closed state. For example, cables 300a and 300b may wrap around features of fastener 200 configured to pivot jaws 203, 205 relative to one another. Said features may be, for example, pulley cams that are formed into jaws 203, 205 of fastener 200. Cables 300a and 300b may return to a proximal location (e.g., coupled to components of handle 50) that allows application of a tensioning force on cables 300a, 300b, and said features of fastener 200 may translate the applied tension into torque/radial motion of jaws 203, 205. Therefore, by tensing or relaxing cables 300a, 300b, fastener 200 may be opened or closed as desired by the user. This may allow the user to repeatedly readjust the positioning of fastener 200, even after fastener 200 has been closed onto tissue and before completely releasing fastener 200 from adapter 100.

Cables 300a and 300b further include, respectively, frangible portions 310a and 310b. For example, the portions of cables 300a and 300b that are routed around pivots 210a, 210b that are thinner or otherwise configured to break upon application of force may represent frangible portions 310a, 310b. Frangible portion 310a, 310b may pull against fastener 200, thereby causing jaws 203, 205 to pivot relative to one another. In some examples, frangible portions 310a, 310b may be thinner portions of cables 300a and 300b more susceptible to breaking than other portions of cables 300a, 300b. Additionally or alternatively, frangible portions 310a, 310b may include linkages, e.g., welded and/or bonded connections, that are configured to break at a specified force or threshold force. It is noted that one or more portions of fastener 200 around which cables 300a, 300b are routed may be frangible as well.

The presence of frangible portions 310a and 310b enables a user to release and deploy fastener 200 from adapter 100 by applying a sufficient tension force to cables 300a and 300b. The amount of tension force sufficient to break frangible portions 310a, 310b from cables 300a, 300b may be greater than the tension force used to transition fastener 200 to a closed state. Thus, frangible portions 310a and 310b remain intact while fastener 200 is in an open state, and fastener 200 transitions to a closed state prior to it being deployed. Once frangible portions 310a and 310b of cables 300a, 300b are broken, pivots 210a, 210b translate radially outwards and away from pegs 110a, 110b of adapter 100. Simultaneously, cables 410, 420 of hoop 400 may translate proximally and revert to a biased position, thereby releasing themselves from hooks 240a, 240b of fastener 200. Thus, fastener 200 reverts to its default, flat state and is released and deployed from adapter 100.

Referring to FIGS. 1-2B, an example of a method of applying a fastener, e.g., fastener 200, is further discussed. A user may couple or mount fastening component 10 to a distal end of sheath 40 or shaft 30 of medical device 1. Fastening component 10 may include fastener 200 mounted onto adapter 100 in an arched and open state. A user may deliver component 10 into the body of a subject, e.g., via a natural orifice (such as a mouth or anus) and through a tortuous natural body lumen of the subject, such as an esophagus, stomach, colon, etc. A user may direct fastening component 10 to an intended target site of tissue, optionally guided by imaging provided by imager 32. Once the target site is reached, a user may engage actuators of handle 50 to apply tension to cables 300a, 300b, thereby closing fastener 200 onto tissue at the target site. A user may also reposition fastener 200 by releasing tension on cables 300a, 300b, thereby re-opening fastener 200 in order to move component 10 to a different position relative to the target site. The user then may re-apply tension onto cables 300a, 300b to close fastener 200 onto the new site. Once secured onto the desired target tissue, the user may apply increased tension onto cables 300a, 300b until frangible portions 310a, 310b are broken, and fastener 200 is released from adapter 100 and deployed onto the site in its default, flat (closed) state.

Figure 3A:
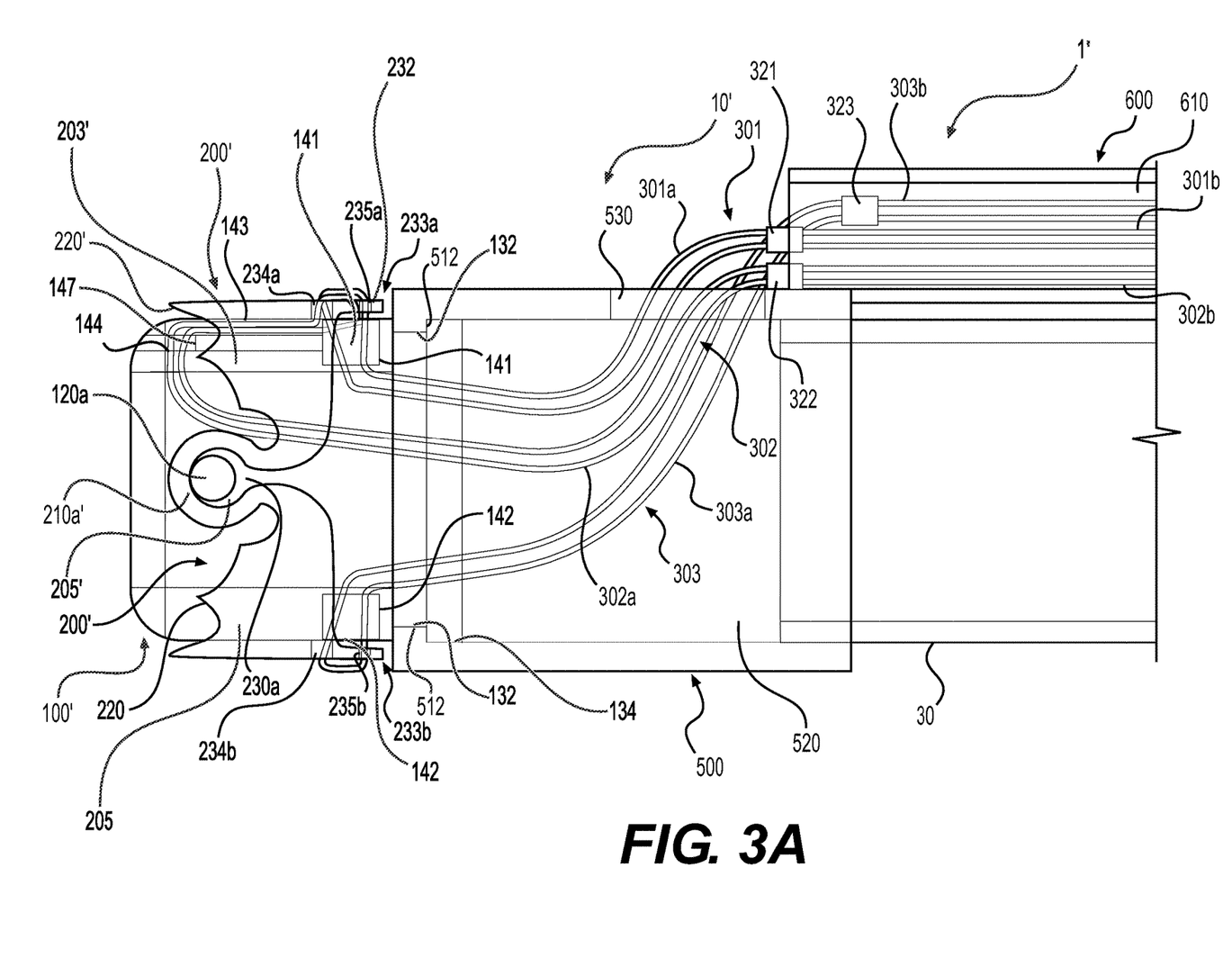
FIG. 3A is a cross-sectional view of a distal portion of a medical device, according to some aspects of this disclosure.
Figure 3B:
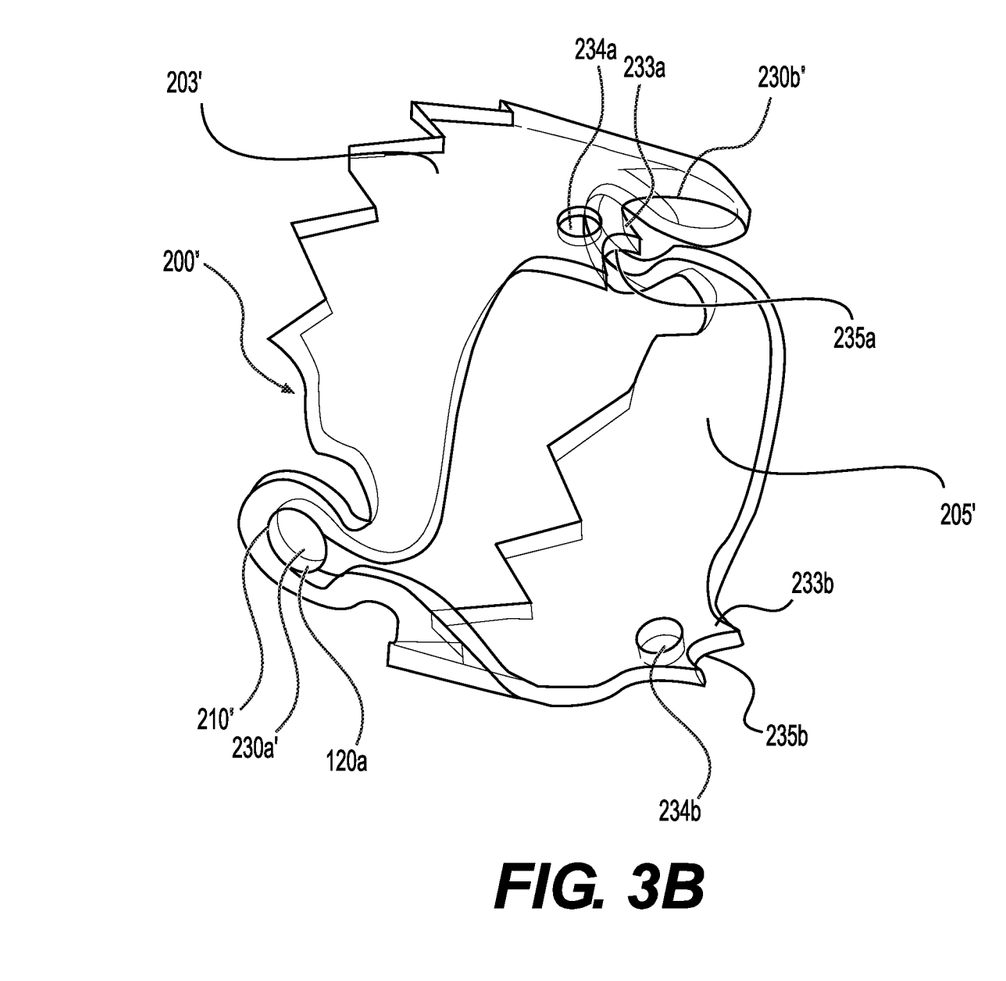
FIG. 3B is a perspective view of the fastener of the medical device of FIG. 3A.

Referring to FIGS. 3A-3B, another example of a fastening component 10' including fastener 200' is shown. In this example, like reference numerals refer to similar features described above in connection to fastening component 10, wherein fastening component 10' and medical device 1' may include any of the features of fastening component 10 and medical device 1. Medical device 1' includes shaft 30 coupled to fastening component 10'. Shaft 30 may be any suitable biocompatible and flexible shaft. Shaft 30 includes a lumen, which may serve as a working channel through which any suitable accessory device or imager may extend therethrough. As shown, shaft 30 includes a protrusion, e.g., lip 42 that extends circumferentially and protrudes radially inward, towards a central axis of shaft 40'. Lip 42 is configured to engage and secure a proximal portion of adapter 100', as discussed in further detail below.

Fastening component 10' includes a connector 500, adapter 100', fastener 200', and cables 301, 302, and 303. In some examples, fastening component 10' also includes a tube 600, as discussed below. Connector 500 as shown is tubular in shape, and includes a lumen 520 between its proximal and distal openings. Connector 500 includes an opening 530 (e.g., in a side of connector 500), which may provide fluid communication between lumen 520 and the external environment. The opening 530 have any suitable shape that provides a passage for cables 301, 302, and 303 to pass through, for example to enter a lumen 610 of a tube 600 as further discussed below. Connector 500 optionally may include guiding components configured to hold and maintain cables 301, 302, and 303 along the inner wall of connector 500.

Tube 600 may be flexible and comprise a biocompatible material. Further, tube 600 may be integrated into connector 500 or coupled to an external surface of connector 500 (e.g., fixed to connector 500 or detachable from connector 500). For example, connector 500 and tube 600 may be a single, integral piece, or may be a separate attachment to connector 500. Tube 600 maybe positioned proximal to opening 530, and the distal end of tube 600 may be adjacent to opening 530. Thus, tube 600 may be positioned relative to opening 530 so that cables 301, 302, and 303 may extend proximally through opening 530 and into lumen 610 of tube 600, towards a handle (further discussed below). In some examples, tube 600 may extend proximally until it reaches a handle component.

It is noted that in some examples, fastening component 10' does not include tube 600 and/or connector does not include opening 530. In such cases, for example, cables 301, 302, and 303 may extend proximally, through the lumen of shaft 30, towards a handle.

Referring again to FIGS. 3A-3B, the proximal opening of connector 500 receives shaft 30 and the distal opening of connector 500 receives adapter 100'. The proximal opening of connector 500 may have as cross-sectional size (e.g., a diameter) configured to receive a distal portion of shaft 30 so that shaft 30 may be securely fitted onto connector 500. For example, connector 500 may be secured onto shaft 30 via a frictional fit. The distal end of connector 500 as shown includes a protrusion, e.g., a lip 512, that extends circumferentially and protrudes radially inward, towards a central axis of connector 500. Thus, connector 500 may be coupled to adapter 100' via lip 512 engaging with a proximal portion of adapter 100', as further discussed below.

Adapter 100' as shown is tubular in shape with a lumen extending along its longitudinal axis. A proximal portion of adapter 100' includes a recess 132 that extends circumferentially about the outer surface of adapter 100'. Recess 132 may be of sufficient depth to receive and engage with lip 512 of connector 500. Thus, adapter 100' may be secured onto shaft connector 500 via the engagement between recess 132 and lip 512. Adapter 100' further includes a first opening 141 and a second opening 142. Openings 141, 142 are on opposite sides of a proximal portion of adapter 100', distal to shaft 30'. Openings 141, 142 are in at least partial alignment with corresponding openings 234a, 234b of fastener 200', and are configured to receive cables 301 and 303, as discussed in further detail below.

The outer surface of adapter 100' further includes a recessed portion defining a channel 143, and a distal edge 147 curved proximally defining a distal passage 144. Channel 143 extends distally from opening 141 to distal passage 144. Distal edge 147 may be a distal portion of adapter 100' onto which cable 302 may rest and apply tension against. Thus, cable 302 may translate or ride on edge 147, similar to a pulley configuration, as cable 302 is pulled proximally. It is noted that the distal portion of adapter 100' may further include a pin, a pulley cam, or another similarly functioning component for cable 302 to ride on, instead of edge 147. Adapter 100' may also further include a pair of projections, e.g., pegs 120a, 120b, protruding radially outwards from a distal portion of adapter 100', e.g., opening 120a. Pegs 120a, 120b are on directly opposite sides of adapter 100', and assist in maintaining fastener 200' onto adapter 100'.

Like fastener 200 of FIGS. 1 and 2A-2B, fastener 200' is also configured to adopt an arched state (as shown in FIGS. 3A-3B) and a default, flat state (similar to FIG. 2A for fastener 200). FIGS. 3A-3B illustrate fastener 200' mounted onto adapter 100' while in an open, arched state. However, unlike fastener 200, fastener 200' is a single piece. The two jaws 203', 205' of fastener 200' may be formed from a single piece of material, wherein the material is molded or shaped to form pivots 210a', 210b' between jaws 203', 205'. In some examples, jaws 203', 205' may comprise a first material, e.g., stainless steel, and pivots 210a', 210b', may comprise a second, different material, e.g., nitinol. In some examples, spring members, e.g., torsional springs, in place of pivots 210a', 210b', may be coupled to jaws 203', 205'.

Each jaw 203', 205' include a plurality of teeth 220' configured to penetrate tissue of a target site. Teeth 220' may be any suitable shape, e.g., pointed, tapered, rounded, straight edged, and/or may include needle pins to anchor to issue. Both pivots 210a', 210b' include central openings 230a', 230b' configured to receive the aforementioned pegs 120a, 120b of adapter 100', thereby allowing fastener 200' to be mounted onto adapter 100'. Fastener 200' may comprise any suitable flexible material, e.g., nitinol, and fastener 200' may be manipulated or adjusted so that fastener 200' is biased to a flat, closed state. Thus, fastener 200' may be held in an arched, open state, against its bias, with the assistance of cables 301, 302, 303, as further described below.

Furthermore, both jaws 203', 205' include respective protrusions 233a and 233b. Protrusions 233a, 233b extend proximally from the proximally facing edges of jaws 203', 205' at the midpoint between pivots 210a' and 210b', while fastener 200' is in an arched, open state. Both protrusions 233a, 233b include cable openings 234a and 234b, respectively, and cable passages 235a and 235b, respectively. Openings 234a, 234b are positioned centrally on protrusions 233a, 233b. Passages 235a, 235b may be defined by the proximal edges of protrusions 233a, 233b, which curve distally), towards openings 234a, 234b. Openings 234a, 234b and passages 235a, 235b are configured to receive cables 301, 302, 303, as discussed below.

Cables 301, 302, and 303 may be any suitable control elements, e.g., sutures including braided sutures, treads, ropes, etc., and may comprise any suitable material(s), including synthetic materials. For example, cables 301, 302, 303 may comprise polyglycolic acid, polylactic acid, monocryl and polydioxanone, nylon, polyester, polyvinylidene fluoride (PVDF), polypropylene, Kevlar, or the like. Cable 301 includes a crimp 321, or any other suitable feature, joining the strands and also the ends of the cable, thereby defining a first loop 301a and a second loop 301b on opposite ends of crimp 321. Cable 301 is routed so that first loop 301a passes through both cable opening 234a, and passage 235a of jaw 203', so that the remaining portion of cable 301, e.g., crimp 321 and second loop 301b, returns proximally towards the handle via opening 141 of adapter 100', lumen 520 of connector 500, and lumen 610 of tube 600.

Likewise, cable 303 includes a crimp 323, which joins both strands and ends of the cable, thereby defining a first loop 303a and a second loop 303b on opposite ends of crimp 323. Cable 303 is also routed so that first loop 303a passes through cable opening 234b and passage 235b of jaw 205', so that the remaining portion of cable 303, e.g., crimp 323 and second loop 303b, returns proximally towards the handle via opening 142 of adapter 100', lumen 520 of connector 500, and lumen 610 of tube 600. Because of such cable routing, proximal tension, e.g., a pulling force, applied to cables 301, 303 causes jaws 203', 205' to pivot relative to one another, thereby transitioning fastener 200' towards an open state. It is noted that jaws 203', 205' may pivot relative to one another simultaneously, but also separately and independently as well by independently controlling the respective cables 301, 303 via actuators of the handle of medical device 1'.

Cable 302 also includes a crimp 322, which joins both strands and ends of the cable, thereby defining a first loop 302a and a second loop 302b, on opposite ends of crimp 322. Cable 302 is routed so that first loop 302a passes through cable opening 234a and passage 235a of jaw 203'. First loop 302a is also routed towards a distal end of adapter 100' via passage through channel 143, over edge 147, and through distal passage 144, before the remaining portion of cable 302, e.g., crimp 322 and second loop 302b, returns proximally towards the handle. The remaining portion of cable 302 may return via a lumen of adapter 100', lumen 520 of connector 500, and lumen 610 of tube 600. Because of such routing, fastener 200' may be deployed from adapter 100' by applying sufficient force and tension onto cable 302. Tension applied to cable 302 (e.g., via a force pulling proximally) results in first loop 302a translating distally along passage 143, while riding against edge 147, which in turn causes first loop 302a to pull on and translate fastener 200' distally relative to adapter 100'. In other examples, fastening component 10' may further include a fourth cable opposite of cable 302, routed through adapter 100' in a similar manner as cable 302. This may provide a more balanced, distal translation of fastener 200' off adapter 100' when both cable 302 and the fourth cable are pulled proximally.

Fastening component 10' of device 1' may be utilized in a similar manner, as discussed above in connection to fastening component 10. For example, after the desired target site is reached, a user may utilize the features of the handle of medical device 1' (similar to features of handle 50 of medical device 1 shown in FIG. 1) to provide slack onto cables 301, 303, thereby closing fastener 200' onto the intended target site. However, prior to providing slack on cables 301, 303, a user may first apply tension onto cable 302 to translate fastener 200' distally along adapter 100', and allow jaws 203', 205' to have a full range of pivoting motion, and avoid obstruction by adapter 100'. A user may re-open or re-close fastener 200' by cycling tension or slack onto cables 301, 303. The user may then apply tension onto cable 302 to release fastener 200' from adapter 100', and deploy fastener 200' onto the site in its default, flat (closed) state. By applying tension to cable 302, cable 302 may assist in translating fastener 200' distally, off adapter 100', via distal surface 147 acting as a pulley or a surface on which force can be applied. It is also noted that a user may apply tension onto cable 302 prior to closing fastener 200' onto tissue for positioning purposes. To release cables 301, 302, and 303 from fastener 200', any portion of first loops 301a, 302a, and 303a may be cut. The user may then pull cables 301, 302, and 303 proximally, resulting in the cut first loops 301a, 302a, and 303a unthreading from the various openings, e.g., opening 234a and passage 235a, of fastener 200'.

Figure 4A:
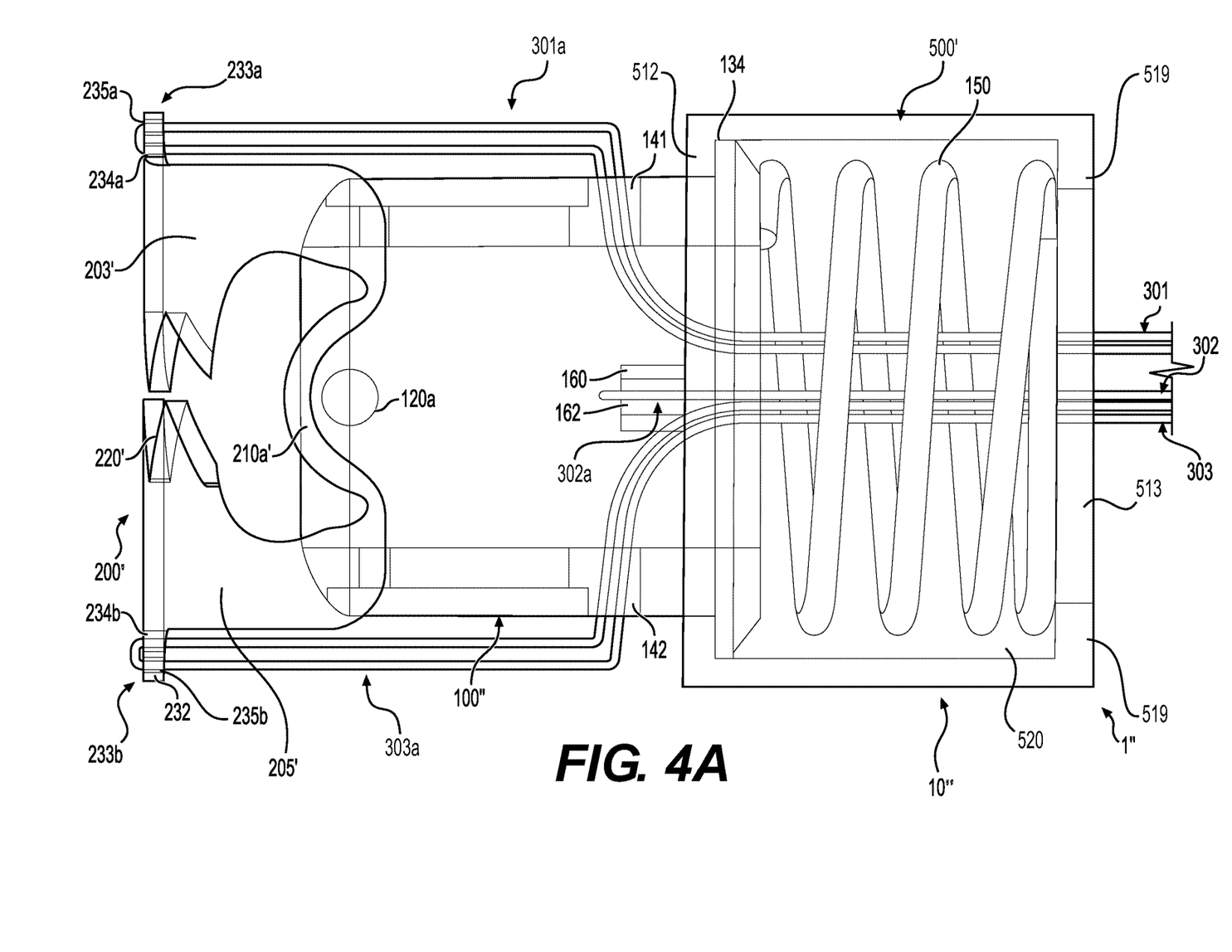
FIG. 4A is a side view of a distal portion of a medical device, according to some aspects of this disclosure.
Figure 4B:
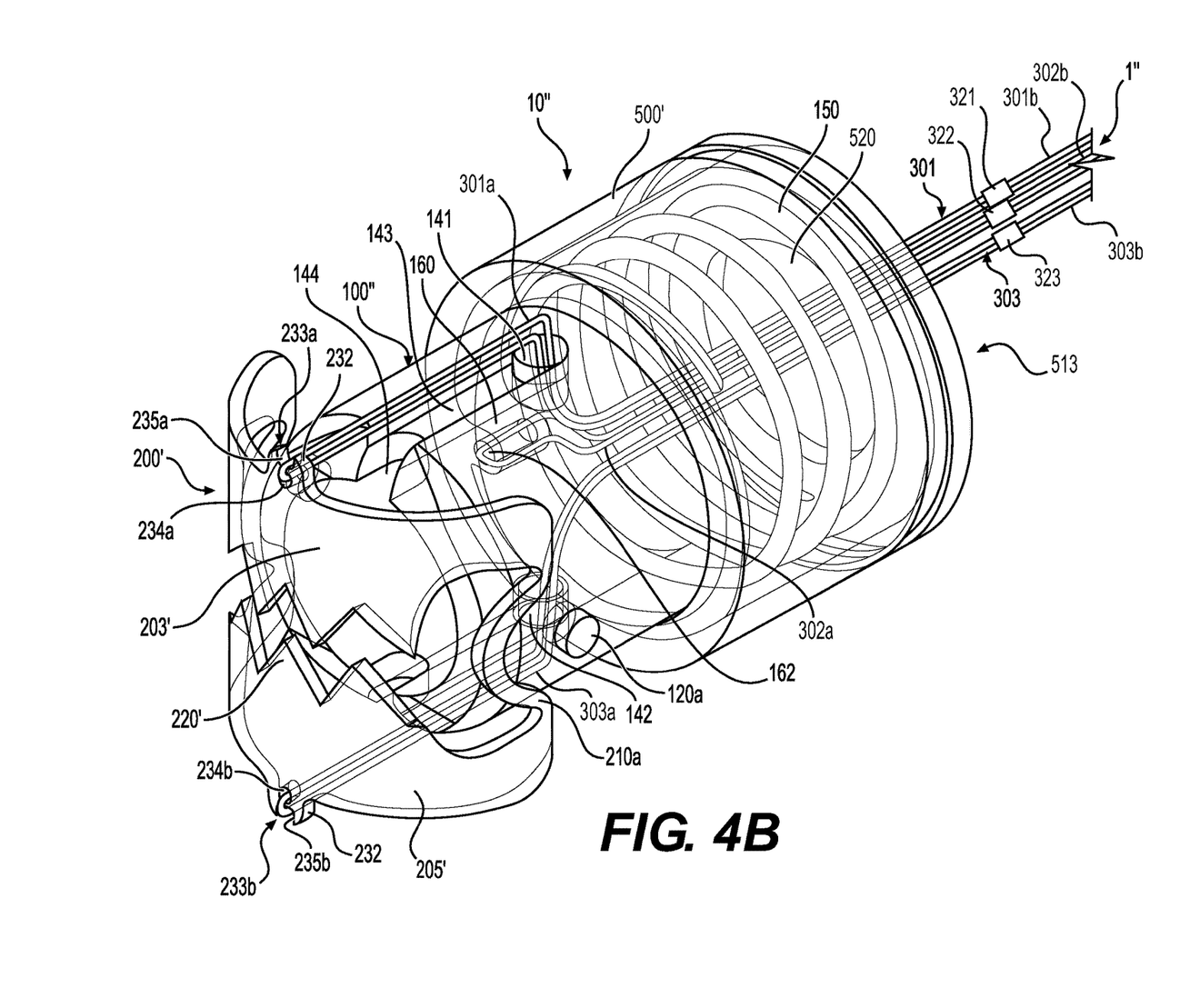
FIG. 4B is a perspective view of the distal portion of the medical device of FIG. 4A.

Referring to FIGS. 4A-4B, another example of fastening component 10" according to the present disclosure is shown. In this example, like reference numerals refer to similar features described above in connection to fastening component 10 and fastening component 10', wherein fastening component 10" and medical device 1" may include any of the features of fastening components 10, 10' and medical devices 1, 1'. FIGS. 4A-4B illustrate fastener 200' in a closed position while mounted onto adapter 100". Adapter 100" is tubular in shape, including a longitudinal opening. A proximal portion of adapter 100" includes an edge 134 that protrudes radially outwards relative to the remainder of adapter 100". Edge 134 extends circumferentially about the outer surface of adapter 100". A proximal portion of adapter 100" may be fitted within the distal opening of connector 500', and edge 134 may abut against lip 512 of connector 500'.

Adapter 100" further includes a tab 160 that protrudes radially inward from an inner surface of adapter 100". Table 160 includes a tab opening 162 configured to receive first loop 302a of cable 302, as discussed in further detail below.

As shown in FIGS. 4A-4B, a spring 150 may be positioned between a distal facing surface of edge 134 and a base 519 residing within lumen 520 of connector 500'. Base 519 protrudes radially inward, along an inner surface of connector 500', towards a central axis of connector 500'. However, base 519 does not protrude to the extent in which it would inhibit or barricade any accessory devices or imagers from extending towards a distal end of connector 500'. Base 519 provides a proximal surface for spring 150 to compress against, when a force is applied against spring 150. Base 519 also defines a proximal opening 513 that is configured to receive a distal portion of a shaft. In some examples, the inner surface of base 519, i.e., the surface facing a central axis of connector 500', may provide friction against a shaft, thereby securing said shaft onto connector 500'. It is noted that FIGS. 4A-4B depict an example of connector 500' without opening 530 or tube 600 (compare to FIG. 3A).

In fastening component 10", first loop 302a of cable 302 is routed around tab 160 of adapter 100", via opening 162. As a result, when tension or pulling force is applied to cable 302, via an actuator of the handle, adapter 100" translates proximally, thereby compressing spring 150. Adapter 100" may be translated proximally until first loops 301a and 303a are caught between shaft 30" and adapter 100", which results in the shearing of first loops 301a and 303a. A distal surface of connector 500' and proximal surfaces of openings 141, 142 may be shearing surfaces.

Fastening component 10" of device 1" may be utilized in a similar manner, as discussed above for fastening component 10'. For example, a user may provide slack onto cables 301, 303, thereby closing fastener 200' onto the intended target site. The user may re-open or re-close fastener 200' by cycling tension or slack onto cables 301, 303. The user may then apply tension onto cable 302, resulting in the proximal retraction of adapter 100" into connector 500', which in turn shears first loops 301a, 303a and releases fastener 200' from fastening component 10".

Figure 5A:
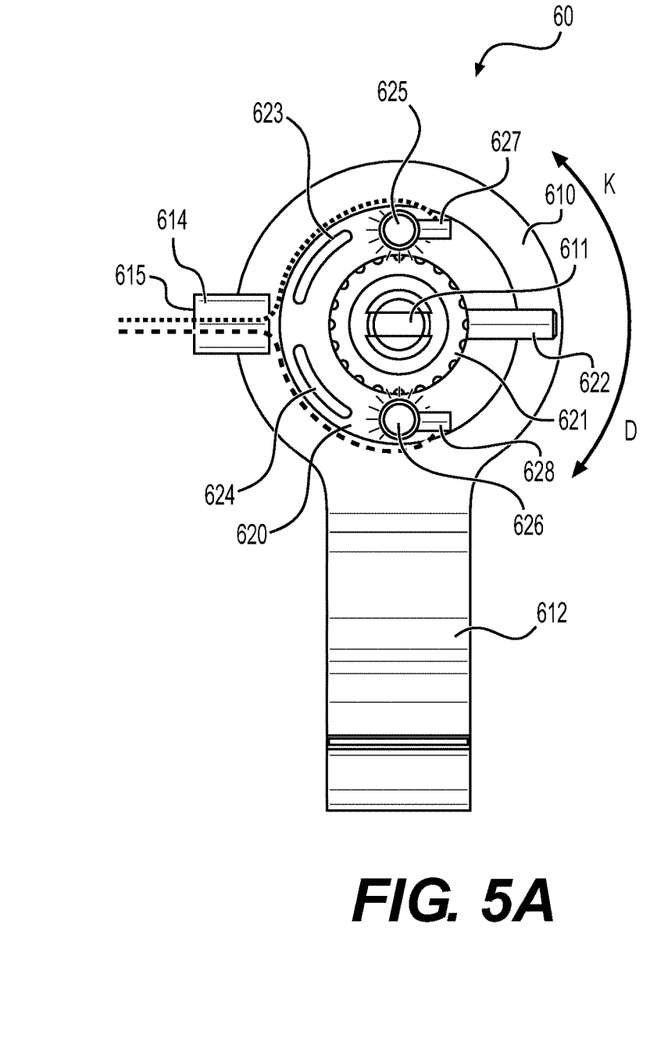
FIG. 5A is a front view of a handle of a medical device, according to some aspects of this disclosure.
Figure 5B:
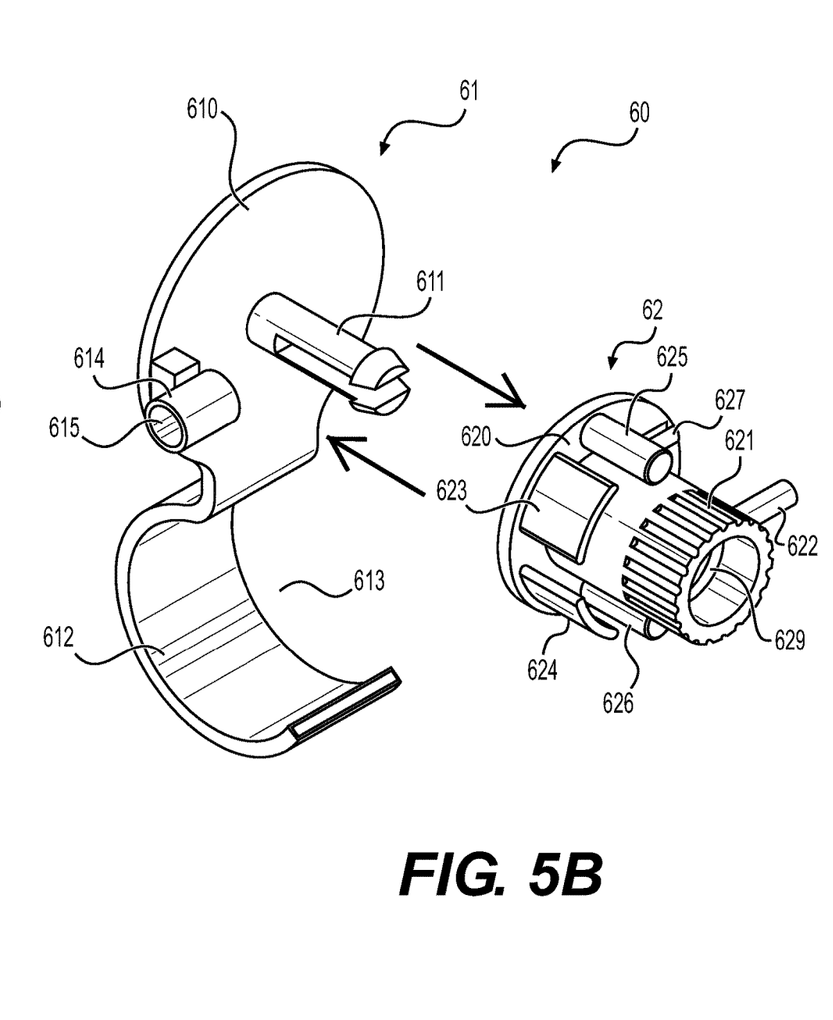
FIG. 5B is a perspective view of the handle of FIG. 5A.

Referring to FIGS. 5A-5B, an example of a handle configured to operate a fastening component according to this disclosure is shown. For example, handle 60 may be used in conjunction with fastening component 10' shown in FIG. 3A and/or fastening component 10" shown in FIGS. 4A and 4B.

Handle 60 includes a base 61 and a wheel 62. Base 61 includes a platform 610 and a clip 612. Platform 610 is planar and circular in shape in the example shown, but may have any other suitable (non-circular) shape. The platform 610 includes an axle 611 that extends perpendicularly from a central part of a planar surface of the platform 610. Axle 611 is configured to receive and hold wheel 62 as shown in FIGS. 5A-5B. For example, axle 611 may be a split fastener axle. It is noted that platform 610 optionally may include a plurality of slots and/or tabs, wherein axle 611 may be maneuvered and positioned within said slots and/or tabs. This may allow various positioning of wheel 62 relative to base 61.

Platform 610 further includes a hub 614 proximate an edge portion of the platform 610. Hub 614 as shown is tubular in shape with lumen 615. Hub 614 may be configured to receive second loops 301b, 302b, and 303b of cables 301, 302, and 303 (see, e.g., FIGS. 3A and 4A-4B) via lumen 615, and route said second loops to wheel 62, as further discussed below. In some examples, hub 614 may engage with an external tube, e.g., tube 600, that provides passage for the aforementioned cables to handle 60. For example, the distal opening of hub 614 may be of a sufficient cross-sectional size (e.g., diameter) to receive or fit within the proximal opening of said external tube (e.g., tube 600). In examples without such an external tube, hub 614 may engage with a proximal port of a shaft, for example, through which second loops 301*b*, 302*b*, and 303*b* may proximally extend. It is noted that in instances when hub 614 is at a distance from an external tube, a secondary tube may be used to bridge the gap between hub 614 and the external tube. Alternatively, second loops 301*b*, 302*b*, and 303*b* may remain exposed until received by hub 614.

Clip 612 may extend from platform 610. Clip 612 may have any suitable features configured to clasp or otherwise hold onto a scope shaft or a scope handle. As shown in FIG. 5B, clip 612 may be a c-shaped clip defining a space 613 that may receive a shaft, e.g., shaft 30 (see FIG. 3A).

Wheel 62 is configured to be rotatably coupled to base 61. Wheel 62 includes a knob 621 that extends perpendicularly from a planar surface 620 of wheel 62. Knob 621 is fixed to said planar surface 620, such that rotation of knob 621 results in simultaneous rotation of wheel 62, relative to platform base 61. Knob 621 includes a crank 622 that extends perpendicularly relative to a longitudinal axis of knob 621. Crank 622 may be any suitable, user-operable handle that assists in rotating knob 621. Wheel 62 also includes a passage 629 extending throughout a length of knob 621 to the surface opposite of planar surface 620. Passage 629 is configured to receive and remain secured onto axle 611, so that wheel 62 is rotatably coupled to base 61.

Wheel 62 further includes a first post 625 and a second post 626, both of which extend perpendicularly from said planar surface 620. First post 625 and second post 626 may be about 180 degrees apart from one another, and each post may be about 90 degrees counter-clockwise/clockwise from hub 614 and crank 622. First post 625 and second post 626 include, respectively, a first protrusion 627 and a second protrusion 628. Protrusions 627 and 628 may extend perpendicularly relative to lengths of respective first post 625 and second post 626. In some instances, protrusions 627, 628 may be configured to receive and secure second loops 301*b*, 302*b*, and 303*b*. However, it is also noted that second loops 301*b*, 302*b*, and 303*b* may be secured onto posts 625 and 626 by any suitable manner, without the assistance of protrusions 627 and 628.

Wheel 62 further includes a first barrier 623 and a second barrier 624. As shown in FIGS. 5A-5B, barriers 623 and 624 may be curved. Barriers 623 and 624 may assist in guiding second loops 301*b*, 302*b*, and 303*b*, along an edge of surface 620, and towards posts 625, 626. Moreover, barriers 623, 624 may define finite lengths or paths, indicated by dashed and dotted lines in FIG. 5A, in which second loops 301*b*, 302*b*, and 303*b* will be displaced when cables 301, 302, and 303 are tensioned. When cables 301, 302, and 303 are slacked, the cables may bow away from barriers 623, 624.

Referring to FIGS. 5A-5B, an example of a manner in which cables 301, 302, 303 are routed around wheel 62, and an exemplary method of using handle 60 is further discussed. While wheel 62 is oriented in the position shown in FIG. 5A, second loop 302*b* (and a fourth cable loop, if present) may be secured to first post 625 and/or first protrusion 627, via the first dotted path. Second loops 301*b* and 303*b* may be secured to second post 626 and/or second protrusion 628, via the second dashed path. In such configuration, wheel 62 does not rotate counter-clockwise, or in the direction of arrow K, since the inner or proximal surfaces of jaws 203', 205' of fastener 200' (see, e.g., FIGS. 3A and 4A-4B) are mounted and abutted to an outer surface of respective adapter 100' or adapter 100". Rotating wheel 62 via knob 622 clockwise, or in the direction of arrow D, pulls second loop 302*b* proximally and translates fastener 200' distally, relative to adapter 100' or 100". Given that fastener 200' is biased towards its closed state, this results in fastener 200' closing and providing slack to second loops 301*b* and 303*b*. After rotation in direction D, rotating wheel 62 via knob 621 in direction K pulls second loops 301*b* and 303*b*, and translates fastener 200' proximally, relative to adaptor 100' or 100". This will also transition fastener 200' towards an open state, and slack the tension of second loop 302*b*. It is noted that the above-described cable routing may also be reversed, such that second loop 302*b* is secured to post 625/protrusion 627, and second loops 301*b*, 303*b* are secured to post 626/protrusion 628, thereby also reversing the directions of knob rotation. Once fastener 200' is in a desired tissue area, and first loops 301*a*, 302*a*, 303*a* are cut or sheared, knob 621 may be rotated in direction K or D, to take up cables 301, 302, 303.

It will be apparent to those skilled in the art that various modifications and variations can be made to the disclosed device without departing from the scope of the disclosure. Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A medical device, comprising:
   a fastener including at least two jaws, wherein the fastener is releasably coupled to an adapter;
   a handle including a wheel;
   a first cable coupled to a first portion of the wheel; and
   a second cable coupled to a second portion of the wheel;
   wherein rotation of the wheel in a first direction is configured to increase tension on the first cable to cause the fastener to move distally with respect to the adapter and to decrease tension on the second cable to close the jaws; and
   wherein rotation of the wheel in a second direction is configured to decrease tension on the first cable to cause the fastener to move proximally with respect to the adapter and to increase tension on the second cable to open the jaws.

2. The medical device of claim 1, wherein the wheel includes a first post and a second post, wherein the first cable is coupled to the first post and the second cable is coupled to the second post.

3. The medical device of claim 2, wherein the wheel includes a first barrier and a second barrier, wherein the first barrier defines a first path for the first cable, and wherein the second barrier defines a second path for the second cable.

4. The medical device of claim 3, wherein the handle further includes a hub configured to receive the first cable and the second cable, route the first cable to the first barrier, and route the second cable to the second barrier.

5. The medical device of claim 2, wherein the first post is separated from the second post by approximately 180 degrees across the wheel.

6. The medical device of claim 1, further comprising a third cable coupled to the second portion of the wheel.

7. The medical device of claim 6, wherein rotation of the wheel in the first direction is configured to decrease tension on the second cable to close the jaws, wherein rotation of the wheel in the second direction is configured to increase tension on the second cable to open the jaws.

8. The medical device of claim 1, wherein a distal end of the first cable is coupled to the adapter, such that rotation of the wheel in a first direction causes the adapter to move proximally with respect to which a shaft to which the adapter is coupled.

9. The medical device of claim 8, wherein continued proximal movement of the adapter is configured to shear the second cable.

10. A medical device, comprising:
- a fastener including at least two jaws, wherein the fastener is releasably coupled to an adapter;
- a handle including a wheel;
- a first cable coupled to a first portion of the wheel;
- a second cable coupled to a second portion of the wheel; and
- a third cable coupled to the second portion of the wheel;
- wherein rotation of the wheel in a first direction is configured to increase tension on the first cable to move the fastener distally; and
- wherein rotation of the wheel in a second direction is configured to increase tension on the second cable to open the jaws.

11. The medical device of claim 10, wherein the wheel includes a first post and a second post, wherein the first cable is coupled to the first post, and wherein the second cable and the third cable are coupled to the second post.

12. The medical device of claim 11, wherein the wheel further includes a first barrier and a second barrier, wherein the first barrier defines a first path that guides the first cable to the first post of the wheel, and wherein the second barrier defines a second path that guides the second cable and the third cable to the second post of the wheel.

13. The medical device of claim 11, wherein the first post includes a first protrusion and the second post includes a second protrusion.

14. The medical device of claim 13, wherein the first cable is coupled to the first protrusion, and wherein the second cable and the third cable are coupled to the second protrusion.

15. The medical device of claim 10, wherein the fastener is releasably coupled to an adapter, wherein rotation of the wheel in the first direction is configured to move the fastener distally relative to the adapter, and wherein rotation of the wheel in the second direction is configured to move the fastener proximally relative to the adapter.

16. A medical device, comprising:
- a fastener including at least two jaws, wherein the fastener is releasably coupled to an adapter, and wherein the adapter is configured to be coupled to a distal end of a shaft;
- a handle including a wheel;
- a first cable coupled to the wheel;
- a second cable coupled to the wheel; and
- a third cable coupled to the wheel;
- wherein rotation of the wheel in a first direction is configured to (a) move the fastener distally relative to the shaft or move the adapter proximally relative to the shaft and to (b) close the jaws; and
- wherein rotation of the wheel in a second direction is configured to (a) move the fastener proximally relative to the shaft or move the adapter distally relative to the shaft and (b) to open the jaws.

17. The medical device of claim 16, wherein continuing to move the adapter proximally shears the second cable and the third cable between the shaft and the adapter.

18. The medical device of claim 16, wherein a distal portion of the first cable is coupled to the adapter.

19. The medical device of claim 16, wherein the wheel includes a first post and a second post, wherein the first cable is coupled to the first post, and the second cable is coupled to the second post.

20. The medical device of claim 19, wherein the wheel further includes a first barrier and a second barrier, wherein the first barrier defines a first path that guides the first cable to the first post of the wheel, wherein the second barrier defines a second path that guides the second cable and the third cable to the second post of the wheel.

\* \* \* \* \*